United States Patent [19]

Hell et al.

[11] Patent Number: 5,633,906
[45] Date of Patent: May 27, 1997

[54] X-RAY COMPUTED TOMOGRAPHY APPARATUS OF THE ELECTRON BEAM TYPE WITH ELECTRON BEAM INTENSITY MEASURING CAPACITY

[75] Inventors: Erich Hell, Erlangen; Manfred Fuchs, Nuremberg, both of Germany

[73] Assignee: Siemens Aktiengesellschaft, Munich, Germany

[21] Appl. No.: 632,385

[22] Filed: Apr. 10, 1996

[30] Foreign Application Priority Data

Apr. 18, 1995 [DE] Germany .................. 195 14 332.9

[51] Int. Cl.⁶ .................................................. H01J 35/30
[52] U.S. Cl. ...................... 378/10; 378/137; 378/138
[58] Field of Search .................. 378/4, 10, 12, 378/119, 121, 137, 138, 145

[56] References Cited

U.S. PATENT DOCUMENTS 4,352,021  9/1982  Boyd ........................... 378/12
5,224,137  6/1993  Plomgren et al. ............ 378/10
5,247,556  9/1993  Eckert et al. ................. 378/4

*Primary Examiner*—Don Wong
*Attorney, Agent, or Firm*—Hill, Steadman & Simpson

[57] ABSTRACT

In an x-ray beam computed tomography apparatus having a ring anode scanned by an electron beam for producing an x-ray beam which rotates around an examination region, measurement of the intensity distribution in the electron beam is enabled at various locations of the ring anode during operation. For this purpose, the ring anode can have at a number of locations around its circumferential direction, insulated sub-anodes with an insulating interspace therebetween, to which a measuring arrangement for measuring the charge distribution, and thus the intensity distribution, in the electron beam is connected. The charge distribution is measured when the electron beam sweeps the interspace between two sub-anodes.

6 Claims, 3 Drawing Sheets

5,633,906

X-RAY COMPUTED TOMOGRAPHY APPARATUS OF THE ELECTRON BEAM TYPE WITH ELECTRON BEAM INTENSITY MEASURING CAPACITY

BACKGROUND OF THE INVENTION

1. Field of the Invention

The present invention is directed to an x-ray computed tomography apparatus, and in particular to such a tomography apparatus of the type wherein the x-ray beam is produced by an electron beam which strikes an annular anode at successive locations around the circumference of the anode to produce a rotating x-ray beam.

2. Description of the Prior Art

In computed tomography (CT), tomograms of a subject are acquired by means of x-rays that pass through the subject and are subsequently registered in a detector system while the x-ray source (or at least the x-ray focus) and the detector are moved along an arcuate path around the subject. For the presentation of moving organs (for example, the heart), the measuring time for a slice of a tomogram must lie clearly below 100 ms. Short scan times (50 ms) can be achieved with electron beam tomography (EBT).

An electron beam tomography apparatus is known wherein a ring anode is provided that is scanned by an electron beam generated by an electron gun in order to generate a rotating x-ray beam. It is thereby necessary that the electron beam intensity be the same at all positions along the ring anode, and in known systems of this type such equal intensity at all positions has either been assumed to exist, or special measures are needed to insure it.

SUMMARY OF THE INVENTION

An object of the present invention is to provided an x-ray tomography apparatus of the EBT type wherein measurement of the electron beam intensity, particularly of the intensity distribution, is made at specific locations of the ring anode.

The above object is achieved in accordance with the principles of the present invention in an x-ray computed tomography apparatus having an annular x-ray source surrounding an examination field, the annular x-ray source including a ring anode which is scanned by an electron beam for producing a rotating x-ray beam, and wherein the ring anode, at a number of locations around its circumferential direction, which measuring means for acquiring the charge distribution in the electron beam. The measuring means in one embodiment are connected for acquiring the charge distribution of the electron beam, as a measure of its intensity, when it sweeps an interspace between two neighboring sub-anodes, and in another embodiment are connected for acquiring the change distribution as the electron beam sweeps a measuring wire disposed over the surface of the anode.

DESCRIPTION OF THE PREFERRED EMBODIMENTS

Figure 1:
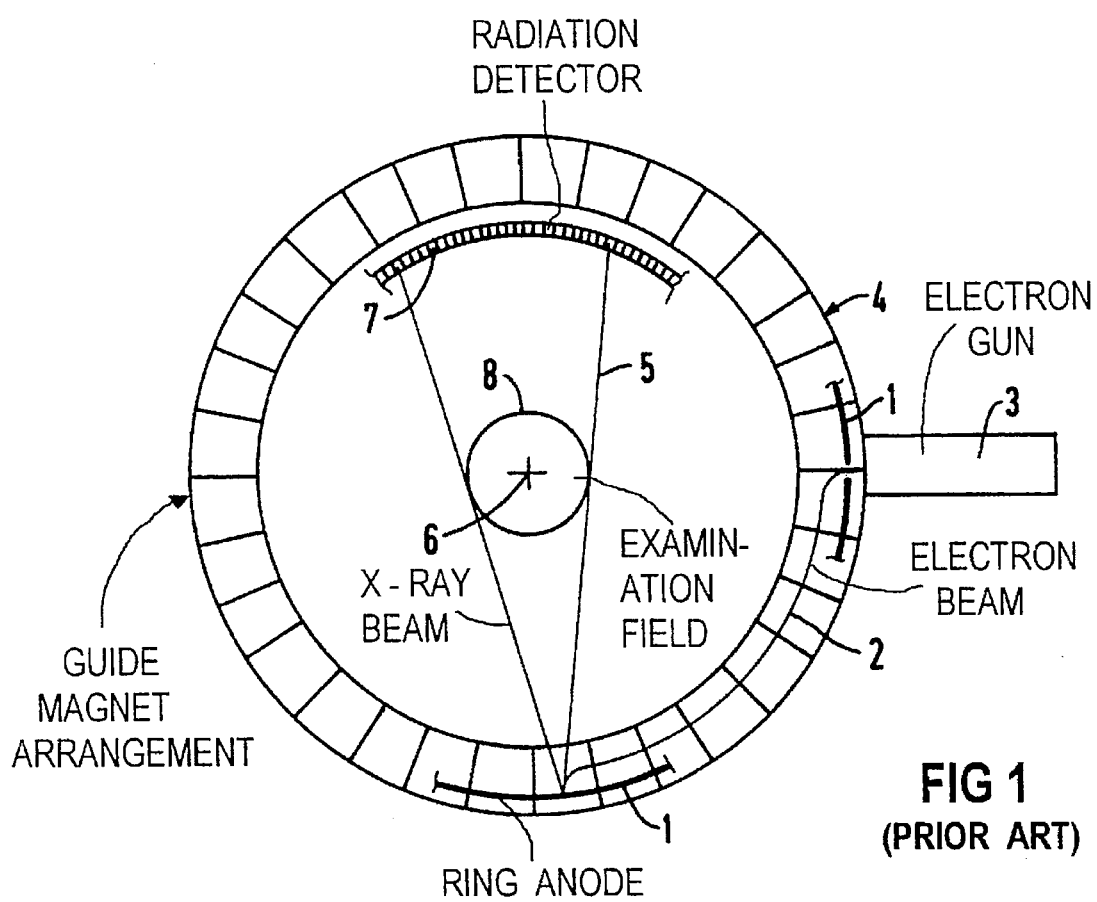
FIG. 1 shows the basic parts of a conventional electron beam tomography apparatus for explaining the idea of the invention.

FIG. 1 shows a portion of the x-ray source of an x-ray computed tomograph in the form of a ring anode 1 contained in a vacuum tube. The ring anode 1 is scanned by an electron beam 2 that is generated by an electron gun 3. An annularly fashioned magnet arrangement 4 circularly guides the electron beam and kicks it onto the ring anode 1. An x-ray beam 5 emanates from the respective focus (point of incidence of the electron beam 2 on the ring anode 1), this x-ray beam 5 being gated fan-shaped in a known way and rotating around the system axis 6 as the focus rotates. The x-ray beam 5 penetrates an examination filed 8 and the attenuated x-rays are incident on an annular radiation detector 7 that generates electrical signals corresponding to the received radiation intensity and supplies them to a computer that generates an image of a patient arranged in the examination field 8 therefrom. In order to permit the x-ray beam 5 to pass the radiation detector 7 when emerging from the vacuum tube, the radiation detector 7 is arranged at the side next to the beam exit window.

Figure 2A:
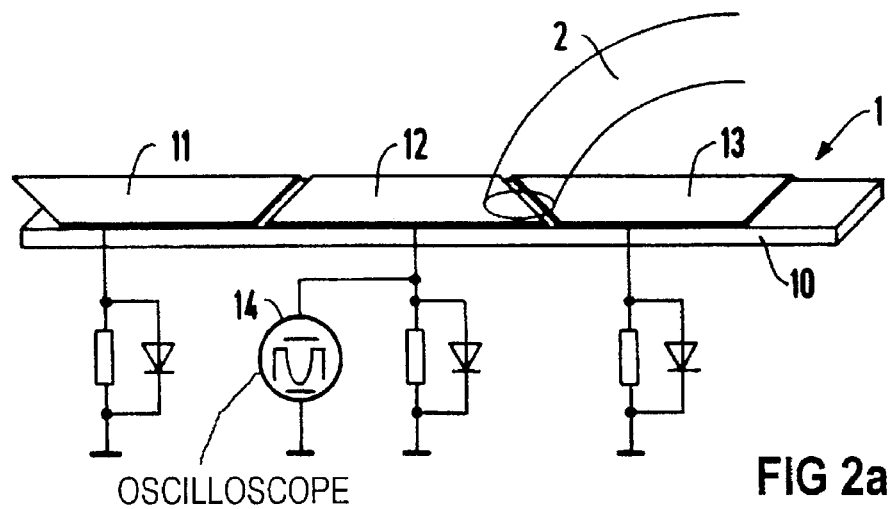
FIG. 2a shows a first embodiment of components which can be provided in the tomography apparatus shown in FIG. 1 for measuring the intensity distribution, shown in FIG. 2b, of the electron beam, in a first embodiment in accordance with the principles of the present invention.
Figure 2B:
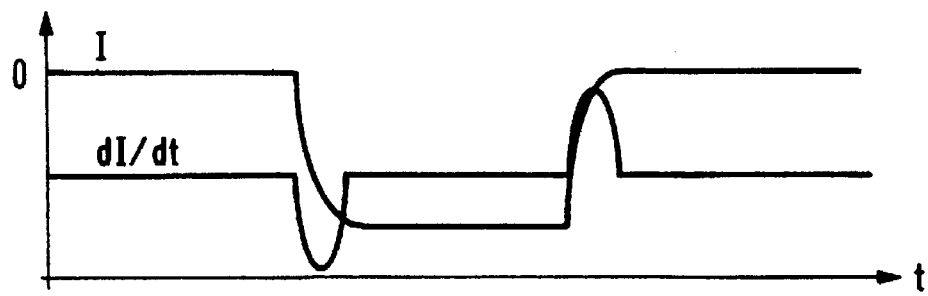

FIG. 2a shows a portion of the ring anode 1. The ring anode 1 has sub-anodes 11, 12 and 13 at a number of locations on an insulating carrier 10, following one another (in this embodiment) in the circumferential direction of the ring anode 1 with a slight interspace between neighboring sub-anodes. Measuring means for measuring the charge distribution in the electron beam 2 are connected with which the charge distribution of the electron beam 2 as it sweeps an interspace between two sub-anodes 11, 12, or 12, 13, is acquired. The connection to an oscilloscope 14 shown in FIG. 2a that displays the distribution I (shown in FIG. 2b) of the beam intensity within the electron beam 2 when sweeping an interspace is provided for this purpose. The oscilloscope 14 can also display the first derivative d I/dr, as also shown in FIG. 2b. The components 10 through 13, of course, are also insulated from the housing of the x-ray source.

Figure 3A:
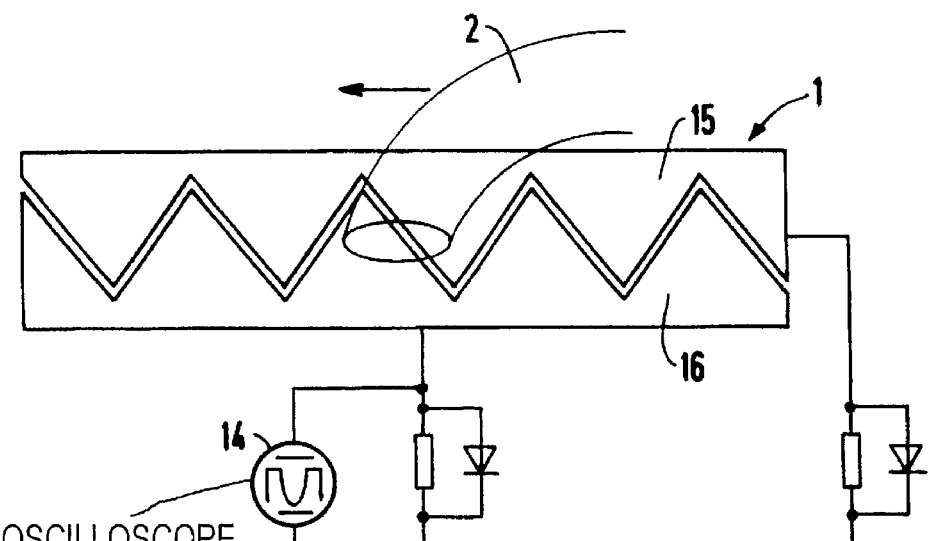
FIG. 3a shows components which can be provided in the tomography apparatus shown in FIG. 1 for measuring the intensity distribution, shown in FIG. 3b of the electron beam, in a second embodiment in accordance with the principles of the present invention.
Figure 3B:
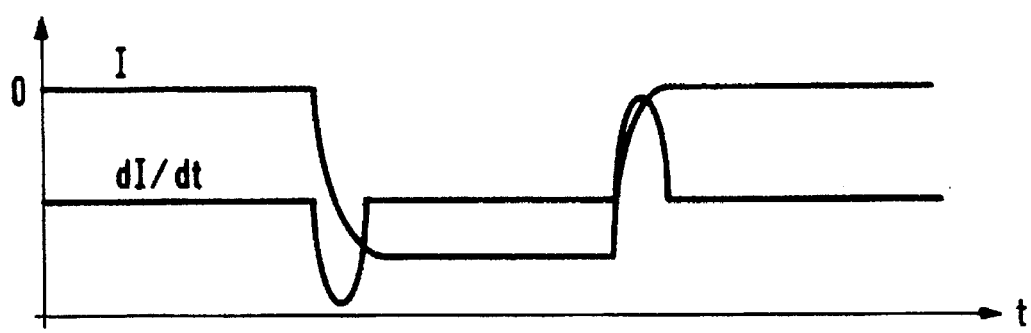

FIGS. 3a and 3b show an embodiment wherein the ring anode 1 has two meshed sub-anodes 15 and 16 at a number of locations of its circumference. The sub-anodes 15 and 16 are meshed in sawtooth fashion with the adjoining edges of the sub-anodes 15 and 16 proceeding obliquely relative to the circumferential direction of the ring anode 1, as in the embodiment of FIG. 2. The sub-anodes 15 and 16 are electrically insulated from one another and from the housing of the x-ray source.

Figure 4:
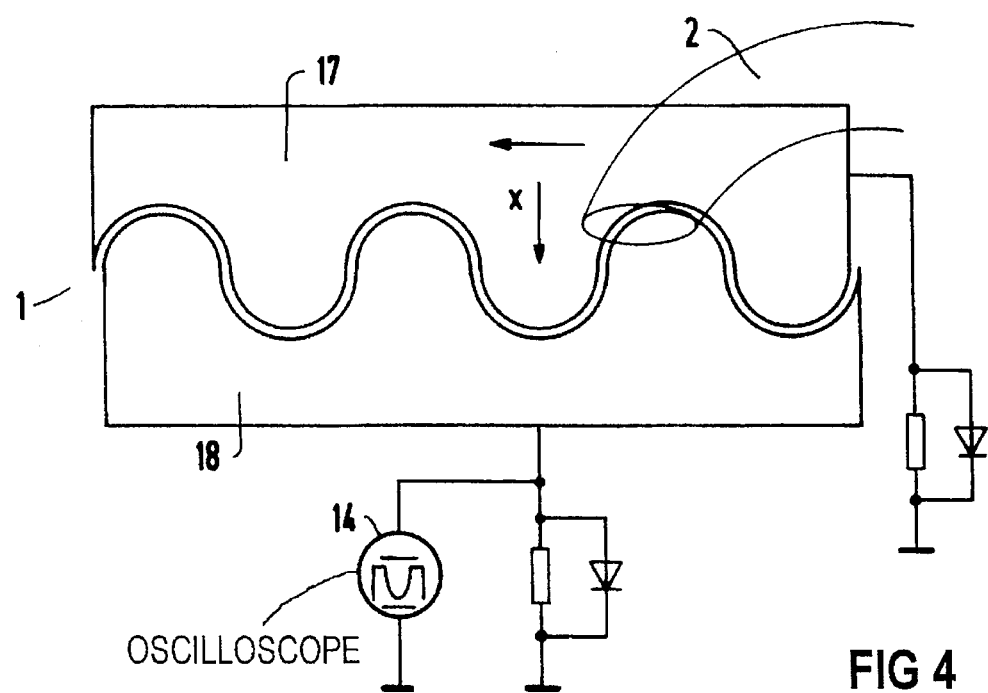
FIG. 4 shows components which can be provided in the tomography apparatus shown in FIG. 1 for measuring the intensity distribution of the electron beam, in a third embodiment in accordance with the principles of the present invention.

The embodiment of FIG. 4 differs from the embodiment of FIG. 3 in that the subanodes 17 and 18 of that embodiment are meshed in serpentine fashion, particularly semicircularly, instead of being meshed in sawtooth fashion.

Figure 5:
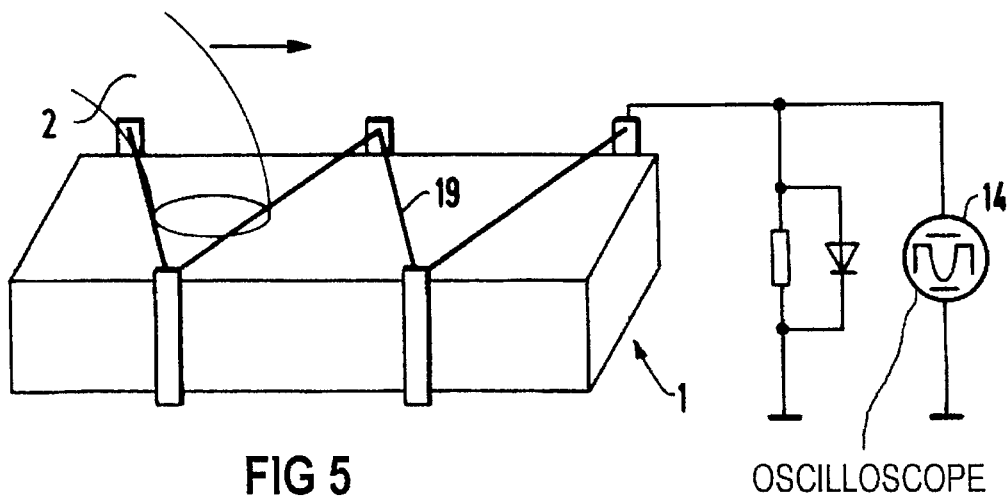
FIG. 5 shows components which can be provided in the tomography apparatus shown in FIG. 1 for measuring the intensity distribution of the electron beam, in a fourth embodiment in accordance with the principles of the present invention.

Instead of using sub-anodes FIG. 5 shows a measuring wire 19 conducted zig-zag, to which the measuring means with the oscilloscope 14 for the charge distribution in the electron beam 2 are connected, for measuring the electron beam charge as it sweeps the measuring wire 19. The measuring wire 19 is extended over the surface of the ring anode 1 at a spacing therefrom and is supported on posts insulated from the ring anode 1. A measuring wire arrangement as shown in FIG. 5 is disposed at each of a plurality of locations of the ring anode 1 distributed over the circumference thereof, thereby permitting the intensity distribution of the electron beam to be acquired at each location.

Although modifications and changes may be suggested by those skilled in the art, it is the intention of the inventors to embody within the patent warranted hereon all changes and modifications as reasonably and properly come within the scope of their contribution to the art.

We claim as our invention:

1. In an x-ray computed tomography apparatus having an annular x-ray source surrounding an examination field, said x-ray source including a ring anode scanned by an electron beam generated by an electron gun for producing an x-ray beam rotating around said examination field, the improvement comprising:

said ring anode having, at least one location, at least two neighboring sub-anodes insulated from each other and separated by an insulating interspace; and measuring means connected to said sub-anodes for measuring a charge distribution in said electron beam as said electron beam sweeps said interspace between said two sub-anodes.

2. The improvement of claim 1 wherein said ring anode has a circumferential direction, and wherein said sub-anodes are disposed successively in said circumferential direction.

3. The improvement of claim 2 wherein said sub-anodes have respective edges adjacent said interspace, said edges extending obliquely relative to said circumferential direction.

4. The improvement of claim 1 wherein said ring anode has two meshed sub-anodes.

5. The improvement of claim 4 wherein said sub-anodes are meshed in sawtooth fashion.

6. The improvement of claim 4 wherein said sub-anodes are meshed in serpentine fashion.

* * * * *